United States Patent [19]
Goldrath

[11] Patent Number: 5,501,691
[45] Date of Patent: Mar. 26, 1996

[54] VERRES NEEDLE SUTURING DEVICE

[76] Inventor: Milton H. Goldrath, 31074 Oakleaf, Frnaklin, Mich. 48025

[21] Appl. No.: 237,402

[22] Filed: May 2, 1994

Related U.S. Application Data

[63] Continuation of Ser. No. 36,074, Mar. 23, 1993, abandoned.

[51] Int. Cl.$^6$ ..................................................... A61B 11/00
[52] U.S. Cl. .......................... 606/148; 606/223; 604/158; 604/164; 604/170
[58] Field of Search .................... 606/103, 144, 606/148, 170, 181, 184, 185, 187, 189, 223; 604/158, 161, 164, 167, 170

[56] References Cited

U.S. PATENT DOCUMENTS

| | | | |
|---|---|---|---|
| 2,416,260 | 2/1947 | Karle . | |
| 2,630,803 | 3/1953 | Baran | 604/158 |
| 3,871,379 | 3/1975 | Clarke . | |
| 4,224,947 | 9/1980 | Fukuda . | |
| 4,808,168 | 2/1989 | Warring | 604/158 |
| 4,842,585 | 6/1989 | Witt | 604/158 |
| 4,869,717 | 9/1989 | Adair | 604/164 |
| 4,935,027 | 6/1990 | Yoon | 606/146 |
| 5,015,250 | 5/1991 | Foster | 606/147 |
| 5,061,238 | 10/1991 | Shuler | 606/170 |
| 5,098,388 | 3/1992 | Kulkashi et al. | 604/158 |
| 5,100,390 | 3/1992 | Lubeck et al. | 604/158 |
| 5,139,485 | 8/1992 | Smith et al. | 604/158 |
| 5,152,769 | 10/1992 | Baber | 606/145 |
| 5,156,596 | 10/1992 | Balbierz et al. | 604/164 |
| 5,183,465 | 2/1993 | Xanthakos et al. | 606/172 |
| 5,281,237 | 1/1994 | Gimpelson | 606/144 |
| 5,334,159 | 8/1994 | Turkel | 604/158 |

FOREIGN PATENT DOCUMENTS

| | | | |
|---|---|---|---|
| 2308346 | 11/1976 | France | 604/158 |
| 3218242 | 11/1983 | Germany | 604/158 |
| WO88/08726 | 11/1988 | WIPO | 604/164 |
| WO90/06783 | 6/1990 | WIPO | 604/164 |
| WO92/11882 | 7/1992 | WIPO | 604/158 |

Primary Examiner—Stephen C. Pellegrino
Assistant Examiner—Jeffrey A. Schmidt
Attorney, Agent, or Firm—Gifford, Krass, Groh, Sprinkle, Patmore, Anderson & Citkowski

[57] ABSTRACT

A Verres needle suturing device. The spring loaded probe of a Verres needle assembly is modified to include an angled guide for guiding the end of a piece of suture material from the channel of the probe out of the opening of the probe so that it can be snared by a snare introduced into the surgical site. The invention is particularly useful for relatively inaccessible surgical sites, such as result from endoscopic and laparoscopic surgery.

9 Claims, 2 Drawing Sheets

VERRES NEEDLE SUTURING DEVICE

This is a continuation of application Ser. No. 08/036,074 filed on Mar. 23, 1993, now abandoned.

FIELD OF THE INVENTION

This invention relates to surgical instruments and, more particularly, to surgical instruments for suturing tissue at a remote surgical site.

DESCRIPTION OF THE RELEVANT PRIOR ART

A wide variety of devices are known for suturing a surgical site. These devices have been developed to assist surgeons in the suturing process, which is both time consuming and difficult due to the precision required, the number of sutures often needed, and the relative inaccessibility of many surgical sites. Access is a particular problem when suturing must be done in a "closed" surgical site, in other words, one resulting from endoscopic or laparoscopic surgery. This type of surgery is performed by using tiny instruments which are inserted through a trocar, an instrument having a hollow sheath with a sharp cutting edge disposed on its end for puncturing and cutting the external tissue over the surgical site. After the incision has been made, the various instruments may be passed through the trocar. Typically, the trocar is used to pierce the external body wall of a patient so that the instruments can be passed into a body cavity of the patient for subsequent surgical manipulation.

Obviously, the "closed" surgical site which results from endoscopic and laparoscopic surgery creates particular problems in suturing since it is even more difficult to access than a typical "open" surgical site. An open surgical site results from conventional surgical methods wherein an appropriately sized surgical incision is made through the tissue of a patient and conventional surgical instruments are used. Nevertheless, even open surgical sites can present problems of access.

A number of solutions to the problems engendered by suturing in both closed and open surgical sites have been proposed. For example, U.S. Pat. No. 4,935,027 discloses a surgical suture instrument with means for remotely controllable suture material advancement. The invention provides for the continuous feed of suture material through opposed forceps jaw members between which the tissue segments are interposed to expedite the suturing process and enables suturing to be accomplished at remote internal sites of the body incident to various endoscopic procedures. While the device disclosed in the '027 may be effective for its stated purpose, it is also very complicated and contains numerous parts, thus rendering it very expensive to manufacture.

U.S. Pat. No. 5,015,250 discloses a needle driver instrument which is used with a trocar sheath for drying a curved suture needle to close microscopic and pelviscopic surgical sites. U.S. Pat. No. 5,152,769 discloses a suturing assembly including a suturing needle having a bore therethrough for forming an arc of thread to be grasped. A rod member secures the arc of thread formed and holds it in place, while the needle forms a second suture and secures the loop as part of the suture. U.S. Pat. No. 3,871,379 also discloses a combined laparoscopic needle and forceps for suturing and ligation of laparoscopic surgical sites. The instruments disclosed in all of these patents are especially fabricated for their special purpose and must be separately manufactured, thus increasing the expense of the surgical procedure. Furthermore, the devices disclosed in these references require that the surgeon be familiar with their operation and add to the multiplicity of instruments already typical of any surgical procedure. Both of these results are undesirable.

It would be advantageous to provide a device to aid in the suturing and ligation of relatively inaccessible surgical sites which is both simple and inexpensive to manufacture and easy to operate. It would be particularly advantageous if such a device represented a modification of existing, widely used surgical devices so as to simplify, rather than make more complex, the surgical procedure.

Verres needle assemblies have been used in the surgical field for over thirty years and are in very widespread use. While there are many commercial brands available, all Verres needle assemblies have certain elements in common: they include a trocar type hollow, cylindrical needle or sheath which terminates in a sharp cutting edge (typically angled) for piercing the external body tissue of a patient. A spring loaded, hollow, gas introducing probe is disposed inside the sheath. The probe includes a cylindrical outer surface, a blunt free end, a longitudinal channel formed through the probe, and an opening onto the outer surface proximate the blunt end of the probe. In all prior art Verres needles, the channel terminates in a blind. The probe portion of the Verres needle assembly moves between a first, extended position, wherein the blunt end projects from the surrounding sheath, to a second, retracted position, wherein the blunt end is substantially disposed inside the sheath. When the probe is in its second, retracted position, the sharp cutting edge of the sheath will cut through the patient's external tissue. On the other hand, when the probe is in its first, extended position, the blunt end will prevent the sheath cutting edge from cutting the patient's internal tissue. Typically, the probe is spring biased into its first, extended position. Thus, when an incision must be made to perform endoscopic or laparoscopic surgery, the assembly will be pushed against the patient's skin, the spring being resilient enough so that the resultant pressure will cause the probe to move to its retracted position, thus permitting the sharp edge of the sheath to pierce the patient's skin and underlying tissue. However, once the device has entered a body cavity underlying the patient's external tissue, the assembly will no longer encounter resistance, and the probe will move back to its extended position, thus preventing the sharp edge of the sheath from doing any further cutting. A Verres needle assembly also includes means for introducing a therapeutic gas into the body cavity through the channel and opening formed in the probe.

In a typical, prior art Verres needle assembly, the channel is simply a straight bore through the probe which is plugged at the tip, with a side opening out onto the cylindrical surface of the probe. Thus, the structure of the Verres needle assembly does not lend itself to introduction of surgical suture material into a surgical incision site since it is virtually impossible to thread a piece of suture material through the channel of the probe and out the side opening. Inevitably, the end of the piece of suture material simply abuts against the inside of the end of the probe and cannot be forced out the side opening.

SUMMARY OF THE INVENTION

The present invention takes advantage of the various capabilities of the Verres needle but eliminates the disadvantage noted above of the prior art Verres needle structure. The present invention is a modified Verres needle assembly which is particularly advantageous for performing suturing of relatively inaccessible surgical sites, such as closed surgical sites. The present invention accomplishes this by modifying the probe of a Verres needle assembly to include an angled guide for directing the end of a piece of suture material from the longitudinal channel of the probe out of the side opening thereof. The angled guide is in communication with both the channel and the opening, and is angled in a direction toward the opening so that the end of the piece of surgical material is directed thereout. Thus, when the piece of suture material is threaded through the modified Verres needle assembly of the present invention, instead of simply and fruitlessly poking against the blocked end of the channel, it will be directed from the channel to the opening via the angled guide.

The angle guide of the present invention may be provided in a modified Verres needle assembly in a variety of ways. For example, it may be molded in a plastic tip which is simply insertable into the open end of the channel. Also, the open end of the channel may be closed off in the conventional manner, and a portion of the channel wall crimped inwardly, thus forming both angled guide and connected opening. Alternatively, the guide may be molded into the channel by filling the end of the channel with a small amount of epoxy or other filler material and allowing it to harden at an angle, thus resulting in an angled guide.

In the method of the present invention, the suturing is performed by inserting a piece of suture material into the probe channel of the modified Verres needle assembly. The suture material is threaded through the channel until the end of the piece projects through the side opening. At that point, the projecting end may simply be caught by means of snare (such as resilient loop, a hook or any suitable configuration) which is also inserted into the surgical site, preferably through a conventional trocar. After the end of the surgical material has been snared, it is then withdrawn from the surgical site, and a knot is tied by using the free ends of the surgical material thus made available. Alternatively, the snare may be inserted into the surgical site as described above, and the tip of the modified probe with the end of suturing material projecting therefrom may be inserted into the snare so that the snare will more readily capture the suture material.

BRIEF DESCRIPTION OF THE DRAWINGS

The following detailed description is best understood by reference to the following drawings in which.

DETAILED DESCRIPTION OF THE PREFERRED EMBODIMENTS

Figure 1:
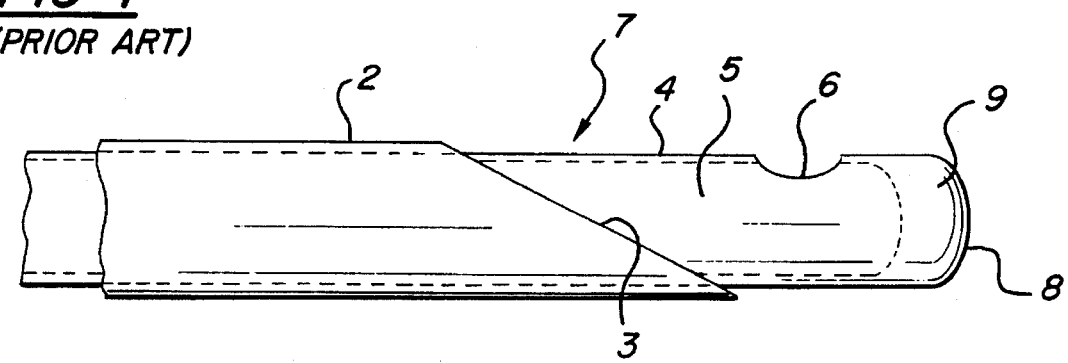
FIG. 1 shows the relevant portion of a typical, prior art Verres needle assembly.

Throughout the following detailed description, like reference numerals are used to identify the same element of the herein invention shown in multiple figures thereof. Referring now to the drawings, and in particular to FIG. 1, there is shown a portion of a typical, prior art Verres needle assembly 7. The prior art needle assembly includes a hollow, cylindrical sheath 2 terminating in an angled sharp edge 3 for puncturing the outer body tissue of a patient (not shown). A spring loaded, hollow, gas introducing probe 4 is disposed inside the hollow sheath 2 and includes a cylindrical outer surface 9, a longitudinal channel 5 formed therein, and a blunt end 8 which terminates the channel 5. An opening 6 is formed on the outer surface 9 of the probe 4 and is in communication with the channel to permit introduction of a therapeutic gas by the Verres needle assembly into internal body structures of the patient.

Like other typical prior art Verres needle assemblies, the probe 4 of the embodiment depicted in FIG. 1 is capable of moving between a first, extended position (as depicted in FIG. 1) wherein the blunt end 8 projects beyond the cutting edge 3 of the sheath 2 to a second, retracted position (not depicted) wherein the blunt end 8 is substantially disposed inside the sheath 2. A prior art. Verres needle assembly is spring biased into the first, extended position but, when the cutting edge 3 is pushed against the skin of a patient undergoing laparoscopic or endoscopic surgery, the force exerted by the skin will cause the probe 4 to move to its retracted position, thereby permitting the cutting edge 3 to cut and penetrate the skin and underlying tissue. However, once these structures have been breached, and the tip of the needle assembly has penetrated into an internal body cavity of the patient, the probe 4 will no longer encounter this resistance and will move back into its first, extended position. The blunt end 8 will then protect the patient's internal body tissue from accidental trauma from the cutting edge 3.

It can readily be seen that the embodiment depicted in FIG. 1 is unsuitable for use as a suturing instrument since any attempt to thread a piece of suture material down the channel 5 will result in the end of the piece of suture material abutting against the inner surface of the blunt end of the probe. It is very difficult, if not impossible, to extract the end of a piece of suture material from the channel through the opening 6.

Figure 2:
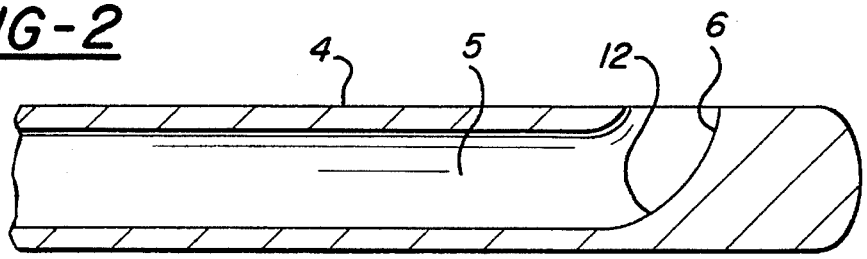
FIG. 2 is a cross-sectional view of the probe of a Verres needle assembly modified according to the present invention.

FIG. 2, which is a cross sectional view of a probe 10 modified according to the teachings of the present invention, shows that an angled guide 12 has been formed in the probe 10. The angled guide 12 connects the opening 6 with the channel 5; the angled guide 12 tapers in a direction toward the opening 6. Thus, when a piece of suture material is threaded through the channel 5 of the modified probe 10, the end of the material will be guided by the angled guide 12 out of the opening 6 where it will be readily available for suturing.

Figure 7:
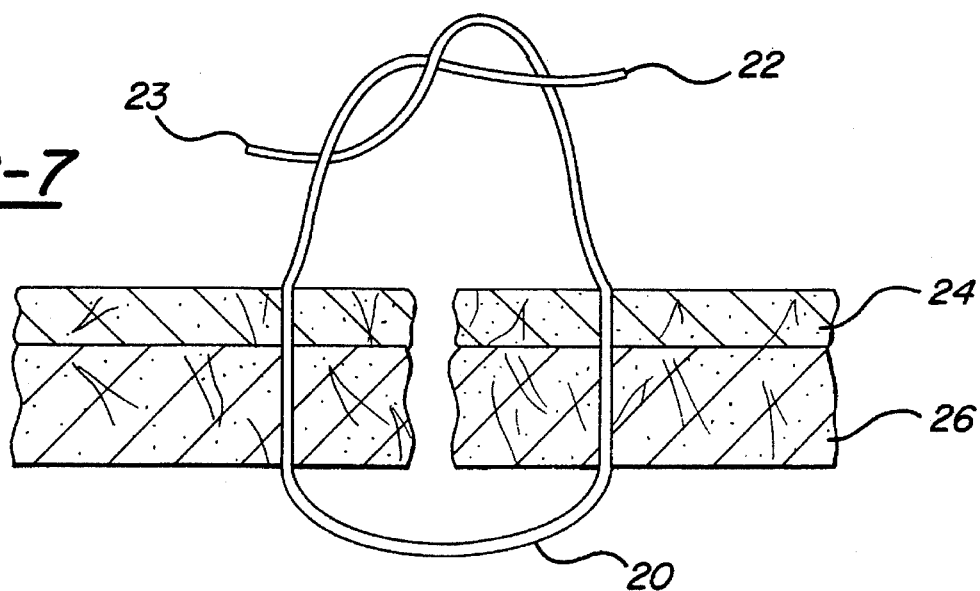
FIG. 7 shows the completion of the suture.
Figure 6:
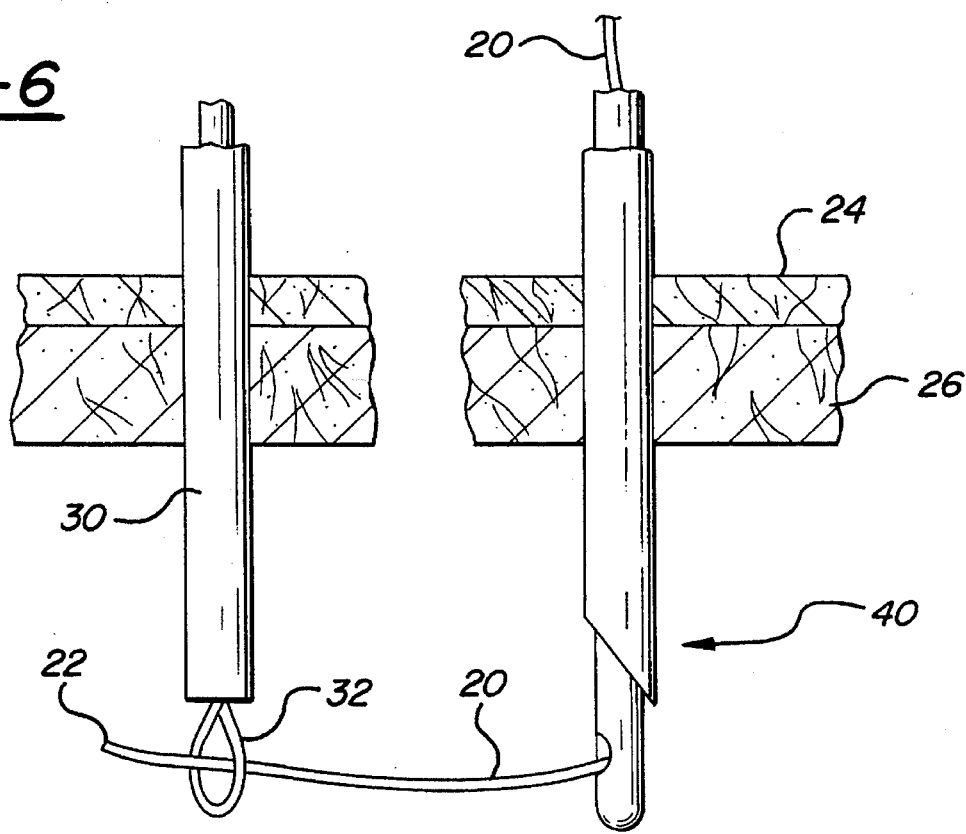
FIG. 6 shows a suture being placed according to the method of the present invention.

FIGS. 6 and 7 illustrate the method of suturing of the present invention. A Verres needle 40 modified according to the teachings of the present invention has been threaded with a piece of suture material 20 having a free end 22. The modified Verres needle 40 has a probe similar to that depicted in FIG. 2. Hence, when the piece of suture material 20 is threaded through the channel of the probe, it will be guided by the angled guide out of the opening and will emerge where it may be grasped by snare 32.

As illustrated in FIG. 6, the modified Verres needle 40 has been introduced into a surgical site through the skin 24 and underlying tissue 26 of a patient. Similarly, a trocar 30 has been introduced into the surgical site by penetrating structures 24 and 26. Snare 32 was passed into the surgical site through trocar 30. After the end 22 of the piece 20 of surgical material has been captured by snares 32, it may be withdrawn from the surgical site through the trocar 30, as has been done in FIG. 7. The modified Verres needle assembly 40 and the trocar 30 and snare 32 may then also be withdrawn from the patient's skin 24 and underlying tissues 26, thus leaving a surgical site with two projecting ends 22, 23 of suture material 20. These ends 22, 23 may then be tied off in the manner depicted in FIG. 7 to suture the surgical site.

Although the snare 32 shown in FIG. 6 is in the form of a loop, it is to be understood that the method of the present invention may be practiced with suture snares of other configurations, including hooks, clamps, etc. The important thing is that the snare be able to capture the free end of suture material introduced through the modified probe of the Verres needle. In some instances, the snare may be fabricated from a material having a shape memory. The snare, in such instances, will include a kink in its shaft proximate the loop portion and when projected from the trocar, the loop of this snare will incline to ward the probe.

In some cases, because the suture material 20 is relatively limp, it may be difficult to capture the free end 22 with the snare 32. Hence, in another embodiment of the method of the present invention, the method may include the step of actually inserting part of the probe of the modified Verres needle assembly into the snare so that it may more easily capture the loose end.

Figure 3:
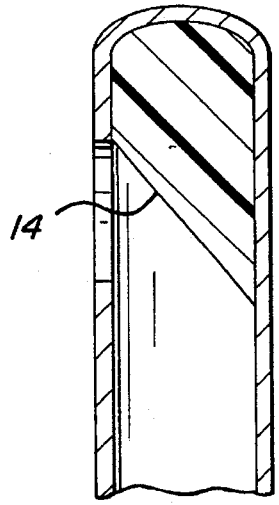
FIGS. 3, 4 and 5 are cross-sectional views which illustrate various alternate embodiments of Verres needle probes modified according to the teachings of the present invention.
Figure 4:
Figure 5:
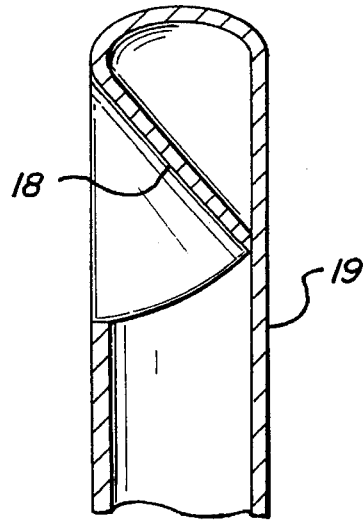

Various embodiments of the angled channel guide of the present invention are shown in FIGS. 3, 4 and 5. In FIG. 3, the angled channel guide is formed by filling the tip end of the probe with a filler material 14, such as epoxy resin. The filler 14 is allowed to harden at an angle to form the angled channel guide.

In the embodiment depicted in FIG. 4, a molded plastic tip 16 which has the angled channel guide end opening molded thereinto is simply inserted into the open channel of the probe of a Verres needle assembly. Since some commercial versions of Verres needle assembly include a plastic tip for plugging the end of the channel, this embodiment is particularly useful to modify those prior art needles.

Yet another embodiment of the present invention is shown in FIG. 5 wherein the angled channel guide is formed by crimping back a portion of sidewall 19 of the probe until it is proximate the internal surface thereof. Crimping back of portion 18 will result in formation of both an angled channel guide and an opening in one manufacturing step.

Of course, while the present invention has been depicted with reference to certain illustrated embodiments and exemplifications thereof, it is not limited by the designs depicted. One of skill in the art may, by reference to the herein specification, achieve other designs by modification of the teachings of the present invention. However, such design modifications are considered to come under the present invention, the scope of which is defined solely by the claims appended hereto and all reasonable equivalents thereof.

I claim:

1. In a needle assembly of the type including:
   a hollow, cylindrical sheath terminating in a sharp cutting edge for piercing external body tissue of a patient; and a spring loaded, hollow, gas introducing probe disposed inside said sheath and having a cylindrical outer surface, a blunt free end, a longitudinal channel formed in said probe, and an opening formed in said surface proximate said blunt free end and spaced apart therefrom, said opening being in communication with said channel so as to permit the passage of gas through said channel, said probe being operative to move between a first, extended position wherein said blunt tip projects from said sheath to prevent said cutting edge from cutting internal body tissue of said patient to a second retracted position wherein said blunt tip is substantially disposed inside said sheath so as to permit said cutting edge to penetrate said tissue, said probe being biased into said first position and operative to move from said first to said second position as the needle assembly penetrates into a body cavity of said patient, the improvement comprising:
   an angled guide connecting said channel and said opening, said guide tapering in a direction toward said opening and including an oblique guide surface operative to guide an end of a piece of suture material which is threaded through said channel out of said opening for subsequent capture by a suture snare.

2. The needle assembly of claim 1 wherein the improvement further comprises said blunt free end including a molded tip inserted into said channel, said tip defining said guide.

3. The needle assembly of claim 1 wherein said probe further comprises a side wall and said angled guide and said opening are defined by a crimped in portion of said side wall disposed proximate said free end and extending in a longitudinal direction opposed therefrom.

4. The needle assembly of claim 1 where said angled guide is formed by a mass of hardened filler material angularly disposed at an end of said channel.

5. A needle assembly for passing a piece of suture material into a surgical site, said needle assembly comprising:
   a hollow, cylindrical sheath terminating in an angled, sharp cutting edge for piercing external body tissue of a patient;
   a spring loaded, hollow probe disposed inside said sheath and having a cylindrical outer surface, a longitudinal channel formed in said probe terminating in a closed, blunt end, and an opening in said surface proximate said end, spaced apart therefrom, and in fluid communication with said channel, said probe being operative to move between a first, extended position wherein said blunt end projects from said sheath to a second, retracted position wherein said blunt end is substantially disposed inside said sheath so as to permit said cutting edge to penetrate said external tissue and introduce said probe and said sheath into a body cavity of said patient;
   biasing means for biasing said probe into said first position; and
   an angled guide connecting said channel and said opening, said guide tapering in a direction toward said opening and including an oblique guide surface operative to guide an end of a piece of suture material threaded through said channel out of said opening for subsequent capture by a suture snare.

6. The needle assembly of claim 5 wherein said closed end of said probe is formed of a molded tip inserted into an open end of said channel said tip defining said angled guide.

7. The needle assembly of claim 5 wherein said probe further includes a side wall, and said opening and said channel are defined by a crimped in portion of said side wall proximate said blunt end and extending in a direction opposed therefrom.

8. The needle assembly of claim 7 where said angled guide is formed by a mass of hardened filler material angularly disposed at an end of said channel.

9. In a needle assembly of the type including:

a hollow, cylindrical sheath terminating in a sharp cutting edge for piercing external body tissue of a patient;

and a spring loaded, hollow, gas introducing probe disposed inside said sheath and having a cylindrical outer surface, a blunt free end, a longitudinal channel formed in said prove, and an opening formed in said surface proximate said blunt free end and spaced apart therefrom, said opening being in communication with said channel so as to permit the passage of gas through said channel, said probe being operative to move between a first extended position wherein said blunt tip projects from said sheath to prevent said cutting edge from cutting internal body tissue of said patient to a second retracted position wherein said blunt tip is substantially disposed inside said sheath so as to permit said cutting edge to penetrate said tissue, said probe being biased into said first position and operative to move from said first to said second position as the needle assembly penetrates into a body cavity of said patient, the improvement comprising:

an angled guide connecting said channel and said opening said guide tapering in a direction toward said opening and including an oblique, planar guide surface operative to guide an end of a piece of suture material which is threaded through said channel out of said opening for subsequent capture by a suture snare.

* * * * *